United States Patent [19]

Strittmatter

[11] Patent Number: 5,396,899

[45] Date of Patent: Mar. 14, 1995

[54] SPINAL PUNCTURE FLUID COLLECTION APPARATUS

[75] Inventor: Warren J. Strittmatter, Durham, N.C.

[73] Assignee: Duke University, Durham, N.C.

[21] Appl. No.: 54,802

[22] Filed: Apr. 28, 1993

[51] Int. Cl.⁶ .............................................. A61B 5/00
[52] U.S. Cl. ..................................... 128/763; 604/403
[58] Field of Search ............... 128/763, 765, 766, 770; 604/403–406; 206/363–365, 370

[56] References Cited

U.S. PATENT DOCUMENTS

| | | | |
|---|---|---|---|
| 3,709,211 | 1/1973 | Hawkins | 128/2 A |
| 3,955,558 | 5/1976 | Fuisz | 128/2 B |
| 3,978,846 | 9/1976 | Bailey | 128/765 |
| 4,024,857 | 5/1977 | Blecher et al. | 128/763 |
| 4,234,095 | 11/1980 | Safianoff | 604/405 |
| 4,430,081 | 2/1984 | Timmermans | 604/256 |
| 4,523,679 | 6/1985 | Paikoff et al. | 206/370 |
| 4,687,479 | 8/1987 | Sarstedt et al. | 604/403 |
| 4,803,999 | 2/1989 | Liegner | 128/763 |
| 5,002,066 | 3/1991 | Simpson et al. | 128/760 |
| 5,046,509 | 9/1991 | Kater | 128/764 |
| 5,059,168 | 10/1991 | Stone | 128/765 |
| 5,069,665 | 12/1991 | Ng | 604/51 |

*Primary Examiner*—Max Hindenburg
*Attorney, Agent, or Firm*—Bell, Seltzer, Park & Gibson

[57] ABSTRACT

An apparatus for performing a spinal puncture on a subject to obtain a sample of cerebrospinal fluid is disclosed. The apparatus operates at ambient pressure. The spinal puncture apparatus is designed to interface with a sample container. A sample container apparatus is also disclosed, as is a kit for use in performing spinal puncture on a subject to obtain a sample of cerebrospinal fluid.

26 Claims, 2 Drawing Sheets

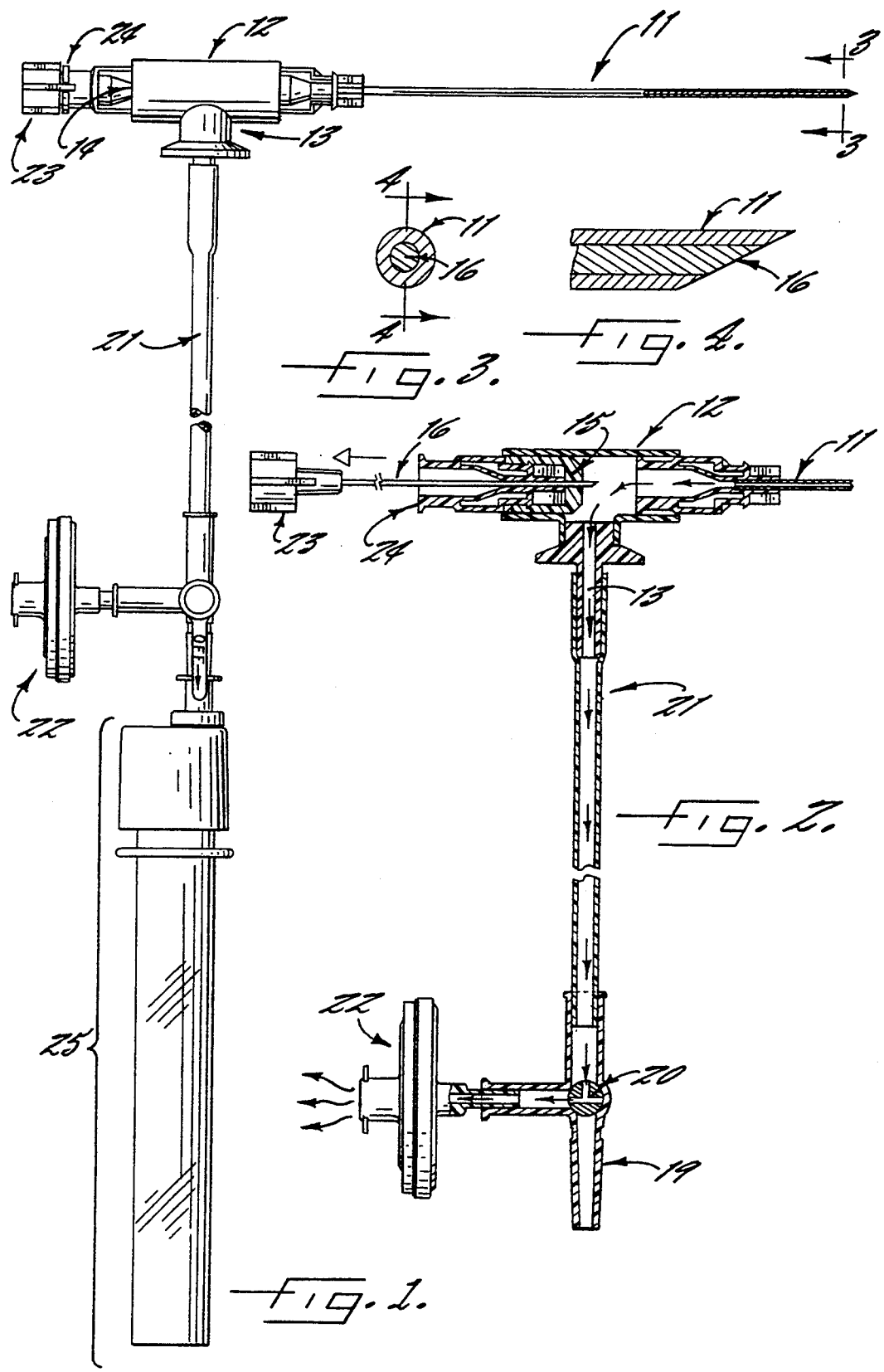

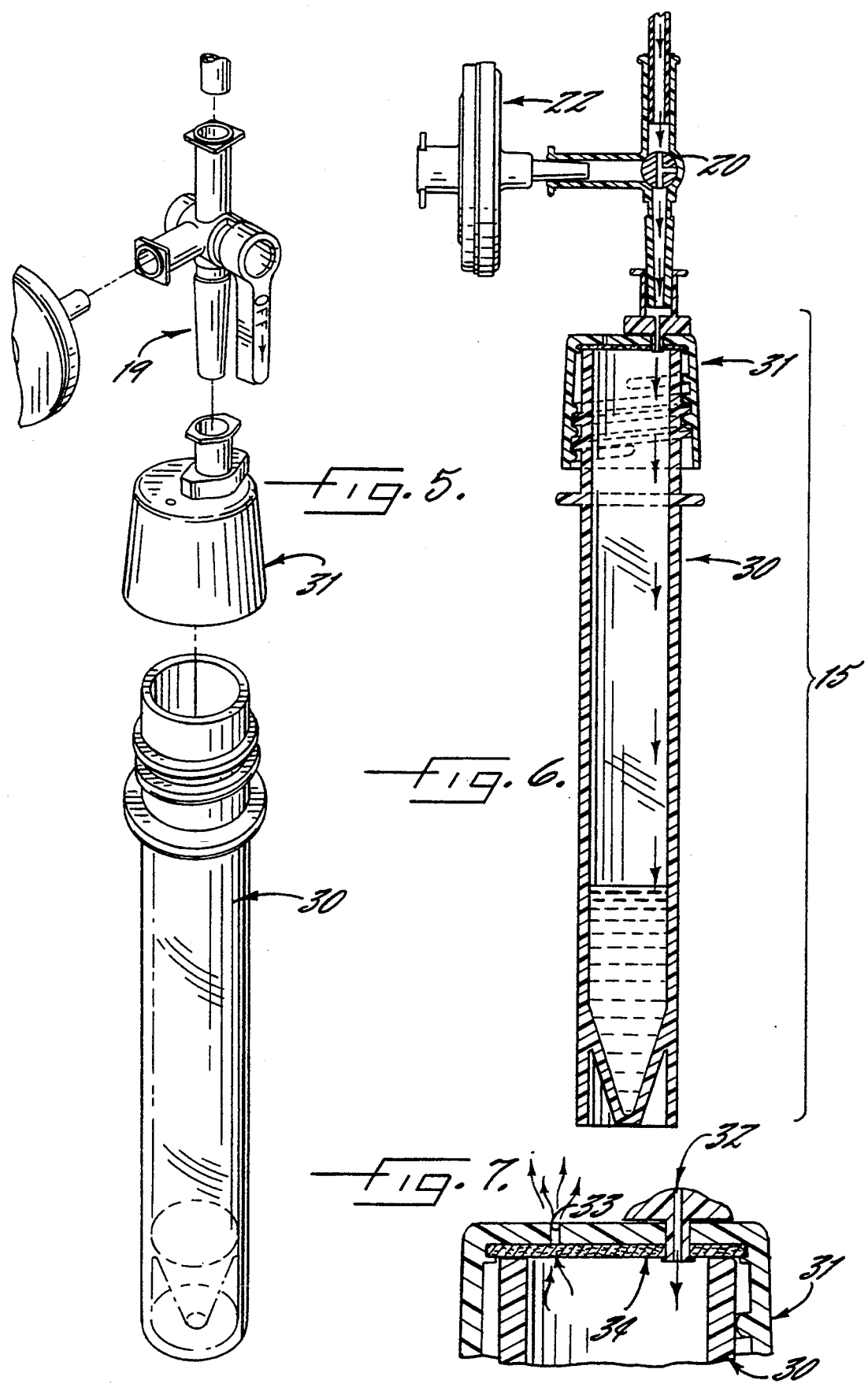

_5,396,899_

SPINAL PUNCTURE FLUID COLLECTION APPARATUS

FIELD OF THE INVENTION

The present invention relates to an improved apparatus for obtaining cerebrospinal fluid samples from a subject and storing such samples.

BACKGROUND OF THE INVENTION

The procedure used to obtain a sample of cerebrospinal fluid is variously called a spinal tap, lumbar puncture, spinal puncture, Quincke's procedure or rachiocentesis. In general, a spinal tap comprises the insertion of a needle into a subject's subarachnoid space of the lumbar region to release cerebrospinal fluid. Cerebrospinal fluid samples may be required for diagnostic purposes, or it may be desirable to release fluid to relieve pressure.

The conventional manner of performing a spinal tap involves, after suitable preparation of the subject, inserting into a lumbar interspace a hollow needle having a distal beveled end. During insertion and extraction the lumen of the needle is typically occluded by a solid stylet which is also beveled at its distal end. The stylet keeps the needle lumen from becoming plugged with tissue during insertion, and prevents tracking of cerebrospinal fluid along the needle pathway (which can lead to infection) during extraction. A hub on the proximal portion of the stylet typically engages with a seat on the proximal portion of the needle to ensure that the distal beveled ends of the stylet and needle are aligned, and to prevent rotation of the fully inserted stylet within the needle lumen.

During a single procedure the stylet may be withdrawn from the needle lumen several times to evaluate whether the needle is within the subarachnoid space; if fluid escapes from the needle lumen the needle tip is in place, if not, the stylet is re-inserted and the needle-stylet combination is repositioned. Once the needle tip is within the subarachnoid space, the stylet is removed and the pressure of the fluid in the subarachnoid space forces fluid out through the needle lumen. To obtain a sample of cerebrospinal fluid conventional sampling techniques require that an open collection vial or other device be held under the hub of the needle to capture fluid as it drips from the needle lumen. Aspiration is typically not used due to potential medical complications in the subject. Contamination of surfaces by dripping cerebrospinal fluid is a frequent occurrence using the conventional cerebrospinal fluid sampling procedure described above. Cerebrospinal fluid can carry pathogens, including the viruses that cause AIDS and hepatitis B.

In view of the foregoing, a first object of the present invention is to provide surgical systems, methods, apparatus for collecting and storing cerebrospinal fluid from a subject.

A further object of the present invention is to provide means for collecting and storing cerebrospinal fluid samples from a subject wherein leakage of cerebrospinal fluid is reduced.

A still further object of the present invention is to provide means for collecting and storing cerebrospinal fluid samples which can be provided to the user in kit form and carried out quickly and conveniently.

SUMMARY OF THE INVENTION

In view of the foregoing, a first aspect of the present invention is a spinal puncture apparatus for collecting cerebrospinal fluid from a patient into a sample container, comprising an elongate hollow spinal puncture needle connected to a junction member. Within the junction member are formed an outlet port which is in fluid communication with the needle lumen, and a stylet port which is longitudinally aligned with the needle lumen. A slidable stylet of a length to extend through the needle lumen, junction member, and stylet port is aligned with the lumen of the needle. Penetrable seal means are connected to the stylet port to prevent fluid flow through the stylet port while allowing the stylet to be slidably moved. A coupling member connected to the outlet port and in fluid communication with the outlet port is configured to connect to a sample container. Valve means are connected to the junction member to block the flow of cerebrospinal fluid from the outlet port to the coupling member.

Also disclosed herein is a sample container for collecting and storing cerebrospinal fluid from a patient. The container comprises a collection vessel having an open end portion and a cap removably attached to the open end portion. An inlet opening and an outlet opening are formed in the cap, and a gas permeable, water impermeable filter is connected to the outlet opening.

The foregoing and other objects and aspects of the present invention are explained in detail in the specification set forth below.

BRIEF DESCRIPTION OF THE DRAWINGS

FIG. 1 is a perspective view of one embodiment of the spinal puncture apparatus with a sample container attached. In this view the stylet is fully inserted in the needle lumen and the graspable hub of the stylet is seated in the hub seat.

FIG. 2 is a cross-sectional view of the spinal puncture apparatus along line 3—3 of FIG. 1. In this view the stylet has been withdrawn from the needle lumen, and the valve is in the "closed" position. The path of fluid flow within the apparatus is indicated by straight arrows; displacement of air through the filter is indicated by irregular arrows.

FIG. 3 is a cross-sectional view of the spinal puncture needle and inserted stylet.

FIG. 4 is a sectional view along line 4—4 of FIG. 3, showing the angled tip of the spinal puncture needle and the corresponding angled tip of the stylet.

FIG. 5 is an exploded perspective view of one embodiment of the sample container and the coupling member of the spinal puncture apparatus to which the sample container is attached.

FIG. 6 is a cross-sectional, perspective view of the sample container, coupling member, filter and valve. Fluid flow from the coupling member through the "open" valve and into the sample container is indicated by straight arrows.

FIG. 7 is a cross-section of the cap of the sample container, depicting fluid flow entering the collection vessel through inlet opening and air displacement from the collection vessel through outlet opening.

DETAILED DESCRIPTION OF THE PREFERRED EMBODIMENT

A preferred embodiment of the present invention is illustrated in FIG. I and FIG. 2. The spinal puncture apparatus comprises an elongate hollow spinal puncture needle (11) with its proximal end connected to a junction member (12). The junction member (12) has formed therein an outlet port (13) and a stylet port (14). The outlet port (13) is in fluid communication with the lumen of the spinal puncture needle, and the stylet port (14) is longitudinally aligned with the spinal puncture needle lumen. A plug formed of SILASTIC TM adhesive or silicone sealant provides a penetrable seal means (15) which is connected to or operatively associated with the stylet port (14) to prevent fluid flow through the stylet port. Of course, those skilled in the art will appreciate that the seal means can be formed of any suitable material, such as natural or synthetic rubber, or could even be a mechanical construct in which insertion of a stylet pushes aside a barrier which would otherwise constrict fluid flow when a stylet is not situated therein. As best shown in FIG. 2, the junction member (12) comprises a hollow tube, with the spinal puncture needle (11) connected to one end and the stylet port (14) formed from the other end, and outlet port (13) formed on the side wall of the junction member.

A stylet (16) is slidably situated within the needle lumen and extends through junction member (12) and through the penetrable seal (15). The stylet is of a length sufficient to extend the entire needle lumen so that the stylet tip and the needle tip may be aligned, as explained in greater detail below.

In one embodiment of the present invention, the proximal end of stylet (16) terminates in a graspable hub (23). The graspable hub may be integrally formed on the proximal end of the stylet, or it may be a separately manufactured piece attached to the proximal end of the stylet. In the preferred embodiment, the stylet port (14) terminates in a hub seat (24) that corresponds to and mates with the graspable hub of the stylet, and hub seat (24) is configured to receive the graspable hub (23) in the aligned position. The alignment of hub (23) and hub seat (24) may be accomplished by forming a tab on hub (23) and a corresponding notch in hub seat (24), or by any suitable means to ensure the consistent alignment of stylet and needle. Stylet (16) is of a length and configuration so that when graspable hub (23) is received in hub seat (24) in the aligned position, the distal end of stylet (16) and needle (11) together form a pointed tip portion, as shown in FIG. 4, having a substantially continuous surface which facilitates penetration and withdrawal of the spinal needle. This pointed tip portion may comprise an angled tip, as shown in FIG. 4, or it may be conical or of any other suitable shape.

A coupling member (19) is connected to the outlet port (13) and is in fluid communication with the outlet port. The coupling member (19) is configured to connect to sample container (25). Any suitable configuration can be employed for the coupling members, with a LUER-LOCK TM coupling currently preferred.

A three-way valve, such as that commercially available from BIO-RAD (Hercules, Calif., USA) provides a valve means (20) which is connected to junction member (12) for controlling sample flow from outlet port (13) to coupling member (19). As will be appreciated by those skilled in the art, many suitable valve means may be employed: the valve may have alternate internal configurations, the valve means may comprise a set of valves, the valve means may be in the form of a bulb or gate rather than a rotatable valve, etc.

A preferred embodiment of the present invention further comprises a gas-permeable, water-impermeable filter (22). Filter (22) preferably comprises a hydrophobic membrane, such as the MILLEX ®-FG filter unit (commercially available from Millipore, Bedford, Mass., USA). In one embodiment, the filter (22) is connected to junction member (12) and is in fluid communication with the needle lumen. More preferably, and as best shown in FIG. 2 and FIG. 6, filter (22) is connected to a three way valve that provides valve means (20). The three-way valve is switchable from a first configuration allowing fluid communication between outlet port (13) and filter (22), to a second configuration allowing fluid communication between outlet port (13) and coupling member (19). One skilled in the art will recognize that any suitable three-way valve may be used to provide valve means (20) in this embodiment.

In a preferred embodiment of the present invention, an elongate flexible tube (21) interconnects outlet port (13) and coupling member (19). The flexible tube allows the spinal puncture needle to be manipulated independently from the coupling member, thus facilitating insertion of the spinal needle in a patient. The flexible tube (21) is preferably made of a substantially transparent material.

A further aspect of the present invention comprises a sample container (25) which can be connected to coupling member (19), as shown in FIGS. 5, 6 & 7. The sample container comprises a collection vessel (30) with an open end and a closed end, and with a removable cap (31) attached to the open end of the collection vessel. Sample container (30) may be any suitable shape and size, but is preferably an elongate tube having an open top portion and an enclosed, conically tapered bottom portion. In a preferred embodiment, cap (31) has an inlet opening (32) and an outlet opening (33). A gas permeable, water impermeable filter (34) is connected to outlet opening (33) to allow the escape of air displaced by fluid flow into the container, while blocking the flow of fluid. Filter (34) is preferably a hydrophobic membrane, such as that employed in the MILLEX® filter commercially available from Millipore, Bedford, Mass., USA.

A still further aspect of the present invention is a kit for use in collecting a cerebrospinal fluid sample from a subject. The kit comprises a sample container and a spinal puncture apparatus, as described above. The kit is preferably contained in a single package, and is most preferably contained in a single sterile package. For example, the kit may comprise a tray having a top of polymeric sheet material sealed thereto, with the components of the kit carried on the tray. The kit may optionally contain instructions for use and additional items such as gauze pads, disinfecting solutions, adhesive bandages, and other materials which would be employed by the clinician in the course of a spinal tap procedure.

In use, the spinal needle is inserted (after suitable preparation of the subject) into a lumbar interspace. During insertion of the needle, the graspable hub of the stylet is seated in the hub seat so that rotation of the stylet within the needle is essentially prevented. The seating of the graspable hub within the hub seat also aligns the needle tip and stylet tip to form a pointed tip having a substantially continuous surface, as shown in FIG. 4, which facilitates penetration and withdrawal of the spinal needle without plugging of the needle during penetration or leaving a "needle track" of extraneous debris in tissue during withdrawal. In a preferred embodiment of the present invention, outlet port (13) and coupling member (19) are connected by an elongate flexible tube (31), allowing the coupling member to be manipulated separately from the spinal needle during use.

During use, when it is thought that the spinal needle has reached the subarachnoid space, the stylet is withdrawn from the lumen of the needle. If the needle tip is in the subarachnoid space the pressure of the cerebrospinal fluid will force cerebrospinal fluid through the needle lumen and into junction member (12). If no fluid enters the junction member, the stylet may be reinserted in the needle lumen and reseated in the hub seat, and the spinal needle repositioned. The procedure is repeated until it is found that the needle tip is properly placed. Once the needle tip is properly placed, the stylet is withdrawn sufficiently to allow cerebrospinal fluid to flow into the junction member.

Fluid flow in a preferred embodiment of the present invention during use, after proper needle placement and removal of the stylet from the needle lumen, is shown in FIG. 2. Due to the existing pressure gradient between atmospheric pressure and pressure within the subarachnoid space, cerebrospinal fluid will flow from the subarachnoid space into the needle lumen, and then into the junction member (12). Penetrable seal means (15), such as a SILASTIC TM plug, prevents fluid flow through stylet port (14); fluid will flow through outlet port (13). When valve (20) is in the "closed" configuration, as shown in FIG. 2, fluid will flow toward filter (22). Air displaced from the interior of the apparatus is forced through the filter while the flow of fluid is blocked by the filter. When valve (20) is switched to its second configuration ("open"), fluid flows through valve (20) to coupling means (19). In a preferred embodiment of the present invention, coupling means (19) is connected to a sample container (25) into which fluid flows. In a more preferred embodiment, coupling means (19) is connected to a sample container as shown in FIG. 5, 6 & 7, which allows fluid to flow through inlet opening (32) into collection vessel (31) as air is displaced through outlet opening (33). Fluid flow through outlet opening (33) is blocked by the gas permeable, water impermeable filter (34), preferably a hydrophobic membrane.

The above elements may be separately formed and joined together by any suitable means. It will be readily apparent to one skilled in the art that forming certain combinations of elements as unitary pieces is equally suitable to practicing the present invention.

In use, after proper preparation and placement of a subject, a sterile kit is opened containing the spinal puncture apparatus and an attached sample container, as shown in FIG. 1. The valve is placed in the "closed" position. The stylet is fully inserted in the needle lumen and the graspable hub of the stylet is aligned with the hub seat and seated. The needle is inserted into a lumbar interspace by an operator until the operator believes the needle tip to be in the subarachnoid space. The operator withdraws the stylet from the needle lumen but does not withdraw the stylet through the SILASTIC TM plug blocking the stylet port. If no cerebrospinal fluid enters the junction member, the stylet is reinserted into the needle lumen and the stylet hub is re-seated on the hub seat. The needle is advanced farther until the operator believes the needle tip is in the subarachnoid space. The stylet is again withdrawn from the needle lumen. If cerebrospinal fluid begins to enter the junction member, cerebrospinal fluid is allowed to fill the spinal puncture apparatus completely, displacing air previously trapped inside the apparatus. The valve is switched to the "open" configuration and fluid is allowed to flow through the coupling member and into the sample container until a sample of a sufficient volume is collected. If more than one sample container of fluid are desired, the valve is then switched to the "closed" position, the filled sample container is disconnected from the coupling member, an empty sample container is connected to the coupling member, and the valve is again switched to the "open" position. Once sample collection is complete, the stylet is reinserted fully in the needle lumen, and the graspable hub is aligned with the hub seat and seated. The needle is withdrawn from the subject.

The foregoing is illustrative of the present invention and is not to be construed as limiting thereof. The invention is defined by the following claims, with equivalents of the claims to be included therein.

That which is claimed is:

1. A spinal puncture apparatus for collecting cerebrospinal fluid from a patient into a sample container, comprising:

an elongate hollow spinal puncture needle having a lumen formed therein;

a junction member connected to said elongate hollow needle, said junction member having an outlet port and a stylet port formed therein, with said outlet port in fluid communication with said lumen and with said stylet port longitudinally aligned with said lumen;

penetrable seal means connected to said stylet port for preventing fluid flow therethrough;

a stylet slidably received in said lumen, said stylet penetrating through said penetrable seal means;

a coupling member connected to said outlet port and in fluid communication therewith, said coupling member configured to connect to said sample container; and valve means connected to said junction member for blocking the flow of cerebrospinal fluid from said outlet port to said coupling member.

2. An apparatus according to claim 1, wherein said junction member comprises a hollow tube having first and second oppositely facing end portions and a side wall, wherein said spinal puncture needle is connected to said first end portion, wherein said stylet port is formed on said second end portion, and wherein said outlet port is formed on said side wall.

3. An apparatus according to claim 1, further comprising an elongate flexible tube interconnecting said outlet port and said coupling member so that said spinal puncture needle and said coupling member may be separately manipulated while said spinal puncture needle is inserted in a patient and said coupling member is connected to a sample container.

4. An apparatus according to claim 3, wherein said elongate flexible tube is substantially transparent.

5. An apparatus according to claim 1, further comprising a gas-permeable, water-impermeable filter connected to said junction member and in fluid communication with said lumen.

6. An apparatus according to claim 1, further comprising a gas-permeable, water-impermeable filter connected to said valve means, and wherein said valve means is switchable between a first position wherein said outlet port is in fluid communication with said filter and a second position wherein said outlet port is in fluid communication with said coupling member.

7. An apparatus according to claim 6, wherein said filter comprises a hydrophobic membrane.

8. An apparatus according to claim 1, wherein:
said needle has a proximal end and a distal end, with said proximal end connected to said junction member and said distal end having an end portion formed thereon;
said stylet has a proximal end and a distal end, with said proximal end having a graspable hub formed thereon, with said distal end having an end portion formed thereon;
said stylet port having a hub seat formed therein configured to receive said graspable hub in an aligned position;
said stylet configured in length so that when said graspable hub is received in said hub seat in said aligned position, said stylet end portion and said needle end portion together form a pointed tip portion having a substantially continuous surface thereon to facilitate penetration and withdrawal of said needle between the spinal vertebrae of a patient.

9. An apparatus according to claim 8, wherein said pointed tip portion comprises an angled tip portion.

10. A spinal puncture apparatus for collecting cerebrospinal fluid from a patient into a sample container, comprising:
an elongate hollow spinal puncture needle having a lumen formed therein;
a junction member connected to said elongate hollow needle, said junction member having an outlet port and a stylet port formed therein, with said outlet port in fluid communication with said lumen and with said stylet port longitudinally aligned with said lumen;
penetrable seal means connected to said stylet port for preventing fluid flow therethrough;
a stylet slidably received in said lumen, said stylet penetrating through said penetrable seal means;
a coupling member connected to said outlet port and in fluid communication therewith, said coupling member configured to connect to said sample container;
an elongate flexible tube interconnecting said outlet port and said coupling member so that said spinal puncture needle and said coupling member may be separately manipulated while said spinal puncture needle is inserted in a patient and said coupling member is connected to a sample container;
valve means connected to said junction member for blocking the flow of cerebrospinal fluid from said outlet port to said coupling member; and
a gas-permeable, water-impermeable filter connected to said valve means, and wherein said valve means is switchable between a first position wherein said outlet port is in fluid communication with said filter and a second position wherein said outlet port is in fluid communication with said coupling member.

11. An apparatus according to claim 10, wherein:
said needle has a proximal end and a distal end, with said proximal end connected to said junction member and said distal end having an end portion formed thereon;
said stylet has a proximal end and a distal end, with said proximal end having a graspable hub formed thereon, with said distal end having an end portion formed thereon;
said stylet port having a hub seat formed therein configured to receive said graspable hub in an aligned position;
said stylet configured in length so that when said graspable hub is received in said hub seat in said aligned position, said stylet end portion and said needle end portion together form a pointed tip portion having a substantially continuous surface thereon to facilitate penetration and withdrawal of said needle between the spinal vertebrae of a patient.

12. An apparatus according to claim 11, wherein said junction member comprises a hollow tube having first and second oppositely facing end portions and a side wall, wherein said spinal puncture needle is connected to said first end portion, wherein said stylet port is formed on said second end portion, and wherein said outlet port is formed on said side wall.

13. An apparatus according to claim 12, wherein said elongate flexible tube is substantially transparent.

14. An apparatus according to claim 12, wherein said filter comprises a hydrophobic membrane.

15. An apparatus according to claim 12, wherein said pointed tip portion comprises an angled tip portion.

16. A spinal puncture kit for collecting cerebrospinal fluid from a patient into a sample container, comprising:
(a) a sample container; and
(b) a spinal puncture apparatus, said spinal puncture apparatus comprising:
an elongate hollow spinal puncture needle having a lumen formed therein;
a junction member connected to said elongate hollow needle, said junction member having an outlet port and a stylet port formed therein, with said outlet port in fluid communication with said lumen and with said stylet port longitudinally aligned with said lumen;
penetrable seal means connected to said stylet port for preventing fluid flow therethrough;
a stylet slidably received in said lumen, said stylet penetrating through said penetrable seal means;
a coupling member connected to said outlet port and in fluid communication therewith, said coupling member configured to connect to said sample container; and
valve means connected to said junction member for blocking the flow of cerebrospinal fluid from said outlet port to said coupling member.

17. A kit according to claim 16, wherein said kit is contained in a single package.

18. A kit according to claim 17, wherein said kit is sterile.

19. A kit according to claim 16, further comprising an elongate flexible tube interconnecting said outlet port and said coupling member so that said spinal puncture needle and said coupling member may be separately manipulated while said spinal puncture needle is inserted in a patient and said coupling member is connected to a sample container.

20. A kit according to claim 16, further comprising a gas-permeable, water-impermeable filter connected to said junction member and in fluid communication with said lumen.

21. A kit according to claim 16, further comprising a gas-permeable, water-impermeable filter connected to said valve means, and wherein said valve means is switchable between a first position wherein said outlet port is in fluid communication with said filter and a second position wherein said outlet port is in fluid communication with said coupling member.

22. A kit according to claim 16, wherein:

said needle has a proximal end and a distal end, with said proximal end connected to said junction member and said distal end having an end portion formed thereon;

said stylet has a proximal end and a distal end, with said proximal end having a graspable hub formed thereon, with said distal end having an end portion formed thereon;

said stylet port having a hub seat formed therein configured to receive said graspable hub in an aligned position;

said stylet configured in length so that when said graspable hub is received in said hub seat in said aligned position, said stylet end portion and said needle end portion together form a pointed tip portion having a substantially continuous surface thereon to facilitate penetration and withdrawal of said needle between the spinal vertebrae of a patient.

23. A spinal puncture apparatus for collecting cerebrospinal fluid from a patient into a sample container, comprising:

an elongate hollow spinal puncture needle having a lumen formed therein;

a junction member connected to said elongate hollow needle, said junction member having an outlet port and a styler port formed therein, with said outlet port in fluid communication with said lumen and with said stylet port longitudinally aligned with said lumen;

penetrable seal means connected to said stylet port for preventing fluid flow therethrough;

a styler slidably received in said lumen, said stylet penetrating through said penetrable seal means;

a coupling member connected to said outlet port and in fluid communication therewith, said coupling member configured to connect to said sample container; and valve means connected to said junction member for blocking the flow of cerebrospinal fluid from said outlet port to said coupling member; and a gas-permeable, water-impermeable filter connected to said valve means, wherein said valve means is switchable between a first position wherein said outlet port is in fluid communication with said filter and a second position wherein said outlet port is in fluid communication with said coupling member.

24. An apparatus according to claim 23, wherein said filter comprises a hydrophobic membrane.

25. A spinal puncture kit for collecting cerebrospinal fluid from a patient into a sample container, comprising:

(a) a sample container; and (b) a spinal puncture apparatus, said spinal puncture apparatus comprising:

an elongate hollow spinal puncture needle having a lumen formed therein;

a junction member connected to said elongate hollow needle, said junction member having an outlet port and a stylet port formed therein, with said outlet port in fluid communication with said lumen and with said stylet port longitudinally aligned with said lumen;

penetrable seal means connected to said stylet port for preventing fluid flow therethrough;

a stylet slidably received in said lumen, said stylet penetrating through said penetrable seal means;

a coupling member connected to said outlet port and in fluid communication therewith, said coupling member configured to connect to said sample container;

valve means connected to said junction member for blocking the flow of cerebrospinal fluid from said outlet port to said coupling member; and a gas-permeable, water-impermeable filter connected to said valve means, wherein said valve means is switchable between a first position wherein said outlet port is in fluid communication with said filter and a second position wherein said outlet port is in fluid communication with said coupling member.

26. A spinal puncture kit according to claim 25, wherein said filter of said spinal puncture apparatus comprises a hydrophobic membrane.

* * * * *